United States Patent [19]

Bonfils et al.

[11] Patent Number: 5,086,040
[45] Date of Patent: Feb. 4, 1992

[54] NOVEL DERMATOLOGICAL COMPOSITION AND METHOD

[75] Inventors: Armelle Bonfils, Conflans Sainte Honorine; Pierre Smets, Villennes sur Seine; René Zalisz, Menucourt, all of France

[73] Assignee: Roussel Uclaf, Romainville, France

[21] Appl. No.: 598,553

[22] Filed: Oct. 16, 1990

[30] Foreign Application Priority Data

Oct. 17, 1989 [FR] France .................. 89-13543

[51] Int. Cl.$^5$ ............................... A61K 7/06
[52] U.S. Cl. ............................. 514/8; 424/401; 424/70; 514/880; 530/825
[58] Field of Search ............... 424/401, 70, 92; 514/880, 8; 435/272, 849, 852, 875, 873, 259; 530/395, 825

[56] References Cited

U.S. PATENT DOCUMENTS 3,929,994 12/1975 Hirsch et al. ................ 424/92
4,699,778 10/1987 Marty ............................ 514/844
4,919,664 4/1990 Oliver et al. .................. 623/15

*Primary Examiner*—Thurman K. Page
*Assistant Examiner*—Amy Hulina
*Attorney, Agent, or Firm*—Bierman and Muserlian

[57] ABSTRACT

A dermatological hair growth stimulating composition containing an effective amount of a glycoprotein extract of gram negative bacteria as the growth stimulant and a method of stimulating hair growth.

2 Claims, No Drawings

NOVEL DERMATOLOGICAL COMPOSITION AND METHOD

STATE OF THE ART

French Patent No. 2,043,475 and its additions Nos. 2,088,112 and 2,171,907 describe glycoprotein extracts of microbial bodies lysed from gram (-) bacteria, the preparation process and their use as medicaments.

OBJECTS OF THE INVENTION

It is an object of the invention to provide novel dermatological compositions and a method of stimulating hair growth.

These and other objects and advantages of the invention will become obvious from the following detailed description.

THE INVENTION

The novel dermatological hair growth stimulating composition of the invention contain an effective amount of a glycoprotein extract of gram negative bacteria as the hair growth stimulant. The compositions demonstrate remarkable hair growth stimulating properties.

Examples of glycoprotein extracts of gram (-) bacteria are preferably the glycoprotein extracts of gram (-) bacteria selected from the group consisting of Klebsiella pneumoniae, Hafnia, Enterobacter cloacae, Escherichia coli, Klebsiella Ozoenae, Pseudomonas aeruginosa and Proteus. Among the glycoprotein extracts of Klebsiella pneumoniae, preferred are the glycoprotein extracts of the Klebsiella pneumoniae strain deposited at the Pasteur Institute in Paris under the No. I-163.

Due to their remarkable properties for stimulating hair growth as illustrated in the experimental part, the glycoprotein extracts of gram (-) bacteria can be used in all forms of alopecia and generally in all occurrences involving temporary and more or less localized hair loss.

The cosmetic or dermatological compositions of the invention contain 0.01% to 0.5% by weight of glycoproteins and preferably 0.02% to 0.1% by weight of glycoproteins.

The cosmetic or dermatological compositions of the invention may be the usual forms used in beauty care such as a cream or gel in pots or tubes, a milk, or an oil, a lotion in glass or plastic bottles and optionally in a dispensing bottle, or also as ampoules. The excipients of the compositions are adapted for application to the scalp.

In fact, for each form, appropriate excipients are used which must have all the qualities usually required. They must be endowed with a high affinity for the skin, be perfectly well tolerated, be stable, be of an adequate consistency to allow easy and agreeable use. Example of excipients in the form of a cream is a mixture of isopropyl myristate, glycerol stearate, soft almond oil, ketyl alcohol and polyol, (respectively 5 g - 15 g - 6 g - 1 g - 5 g for 100 g of distilled water). In the form of a milk, the combination of sorbitan monostearate, polyoxyethyl ketyl ether, vaseline oil, isopropyl palmitate, bees wax and polyol (respectively 1 g - 3 g - 5 g - 5 g - 1 g - 5 g for 100 g of distilled water) is suitable. In the form of a gel, for example, carboxyvinyl polymer combined with triethanolamine is used and an ester of a fatty acid (respectively 3 g - 3 g - 5 g for 100 g of distilled water). For the oil form, the triglycerides of fatty acids combined with perhydrosqualene (respectively 30 g and 20 g for 100 g of vegetable oil).

Optionally, the compositions of the invention can also contain small quantities of sun filters or screens, vitamin extracts, perfumes, preservatives and colorants.

The different cosmetic forms mentioned above can be obtained according to the usual methods employed in this field.

The glycoprotein extracts of gram (-) bacteria can be prepared as indicated in French Patent No. 2,043,475 mentioned previously or in one of its additions. In the experimental part which follows, product A means the glycoprotein extracts of the Klebsiella pneumoniae strain deposited at the Pasteur Institute in Paris under the No. I-163. These glycoproteins have been prepared according to the information given in Example 1 of French addition No. 2,171,907.

The novel method of the invention for stimulating hair growth comprises applying to the hair of a warm-blooded animal, including humans, a composition containing an effective hair growth stimulating amount of a glycoprotein extract of gram negative bacteria. The treatment preferably consists of 2 or 3 applications per day of a cream or gel or cosmetic lotion containing 0.05% of glycoproteins to the scalp or hair to be treated.

In the following examples, there are described several preferred embodiments to illustrate the invention. However, it is to be understood that the invention is not intended to be limited to the specific embodiments.

EXAMPLE 1

A cream was prepared containing the following ingredients:
glycoprotein extract of Klebsiella pneumoniae (Product A): 0.05 g
oleyl acetate: 2.0 g
alkyl phosphate of diethanolamine: 2.0 g
ethylhexyl palmitate: 8.0 g
hydrogenated lanoline: 5.0 g
triglycerides of fatty acids: 4.0 g
sorbitan stearate: 1.0 g
carboxyvinyl polymer: 0.4 g
preservatives: 0.4 g
aromatic composition: 0.4 g
purified water sufficient quantity for: 100 g

EXAMPLE 2

A gel of the following formula was prepared:
glycoprotein extracts of Klebsiella pneumoniae (product A): 0.05 g
Centella Asiatica glycol extract: 5.0 g
propylene glycol: 5.0 g
carboxyvinyl polymer: 0.8 g
preservatives: 0.35 g
aromatic composition: 0.1 g
purified water sufficient quantity for: 100 g

STUDY OF THE STIMULATION OF KERATIN SYNTHESIS IN A RAT

Male Wistar rats 21 days old at the time of the experiment were used in this experiment and in each test, the animals of one group were from the same litter. Each group comprised 6 animals. During the experiment, the animals were kept n a Makrolon cage with 2 to a cage. The animals were divided into two groups of 6 and each animal was treated daily for 7 days out of 7 for 31 days with 0.5 ml of a solution of 500 ug/ml of product A in distilled water or with 0.5 ml of distilled water (control group). On the 10th day of treatment, each animal received by oesophageal probe a single dose of cysteine-$S^{35}$ in the form of a solution of 1 MBq/ml in a solution of 0.9% sodium chloride.

Fur samples were taken at each occasion before the day's treatment. The fur samples were taken with curved-blade scissors from the treated areas and the control areas. A sample of 50+2 mg was weighed and dissolved in 1 ml of toluene with stirring in a water bath for several hours at 70° C. in sealed flasks. After complete dissolution and cooling down, 10 ml of Intagel scintillating liquid was added and measurement of the beta - radioactivity of $S^{35}$ was effected. Each count was done for at least 10 minutes and more if necessary to have a count greater than 1000 pulses, which ensured a statistical accuracy of counts of greater than +3%. The results are shown in the table below.

| | $S^{35}$ activity in d.p.m. for 50 mg of fur from animals treated with product A | | | | | |
|---|---|---|---|---|---|---|
| | Treated | Control | Treated | Control | Treated | Control |
| | Day 11 | | Day 25 | | Day 32 | |
| | 153 | 107 | 9799 | 1830 | 4950 | 4352 |
| | 109 | 88 | 9605 | 1790 | 5680 | 3212 |
| | 142 | 74 | 5079 | 2028 | 4825 | 2100 |
| | 92 | 214 | 8769 | 6743 | 4036 | 2620 |
| | 150 | 105 | 12185 | 2953 | 4883 | 1925 |
| | 127 | 124 | 7612 | 9797 | 3928 | 1937 |
| X | 128 | 118 | 8841 | 4190 | 4717 | 2691 |
| Sx | 9.9 | 20 | 972 | 1360 | 265 | 389 |
| d | 10 | | 4651 | | 2026 | |

| -continued | | |
|---|---|---|
| $S^{35}$ activity in d.p.m. for 50 mg of fur from animals treated with product A | | |
| Treated Control Day 11 | Treated Control Day 25 | Treated Control Day 32 |
| $S_d$  23 | 1672 | 265 |
| t  0.44 | 2.78 | 4.30 |
| | 0.05 | 0.01 |

The results show on D 25, a net incorporation of -$S^{35}$cysteine (+110%) is despite a significant divrgence in individual data, the increase was significant. On D 32, the increase in cysteine -$S^{35}$ incorporation was still more significant (alpha<0.01). Daily observation of the animals show that with those from the treated group, the fur regrows faster after sampling on D 11 and D 25 than with the animals from the control group. Therefore, product A showed a very important and very significant activity on the synthesis of Keratin which was accompanied by accelerated hair growth after cutting.

Various modifications of the method and compositions of the invention may be made without departing from the spirit or scope thereof and it is to be understood that the invention is intended to be limited only as defined in the appended claims.

What we claim is:

1. A method for stimulating hair growth of a warm-blooded animal in need thereof comprising applying to the hair of a warm-blooded animal a composition containing 0.01 to 0.05% by weight of an effective hair growth stimulating amount of a glycoprotein exract of gram negative bacteria selected from the group consisting of Klebsiella pneumoniae, Hafnia, Enterobacter cloacae, Escherichia coli, Klebsiella Ozoenae, Pseudomonas aeruginosa and Proteus.

2. The method of claim 1 wherein the gram negative bacteria is the Klebsiella pneumoniae strain No. I-163 deposited at the Pasteur Institute.

* * * * *